(12) United States Patent
Sharma

(10) Patent No.: US 11,045,340 B2
(45) Date of Patent: Jun. 29, 2021

(54) ADDING ACCESSIBILITY PROPERTIES TO A SOFTWARE APPLICATION

(71) Applicant: INTUIT INC., Mountain View, CA (US)

(72) Inventor: Sundip Sharma, Bangalore (IN)

(73) Assignee: INTUIT INC., Mountain View, CA (US)

( * ) Notice: Subject to any disclaimer, the term of this patent is extended or adjusted under 35 U.S.C. 154(b) by 352 days.

(21) Appl. No.: 15/270,694

(22) Filed: Sep. 20, 2016

(65) Prior Publication Data

US 2018/0032232 A1 Feb. 1, 2018

(30) Foreign Application Priority Data

Jul. 28, 2016 (IN) .............................. 201631025850

(51) Int. Cl.
*A61F 4/00* (2006.01)
*G06F 9/451* (2018.01)
*G06F 3/0481* (2013.01)

(52) U.S. Cl.
CPC .............. *A61F 4/00* (2013.01); *G06F 3/0481* (2013.01); *G06F 9/451* (2018.02)

(58) Field of Classification Search
CPC ........... A61F 4/00; G06F 9/451; G06F 3/0481
See application file for complete search history.

(56) References Cited

U.S. PATENT DOCUMENTS

| 5,583,981 | A | * | 12/1996 | Pleyer | G06F 3/0481 715/201 |
|---|---|---|---|---|---|
| 6,326,934 | B1 | * | 12/2001 | Kinzie | B67D 7/04 340/10.1 |
| 7,792,701 | B2 | * | 9/2010 | Basson | G06Q 30/0601 705/1.1 |
| 8,195,466 | B2 | * | 6/2012 | Carminati | G10L 13/00 341/50 |
| 8,428,657 | B2 | * | 4/2013 | Scott | G10L 13/02 379/433.04 |
| 9,153,227 | B2 | * | 10/2015 | Scott | G10L 13/02 |
| 9,370,299 | B2 | * | 6/2016 | Haine | A61B 3/066 |
| 9,785,336 | B2 | * | 10/2017 | Summers, II | G09B 5/02 |
| 2002/0152255 | A1 | * | 10/2002 | Smith, Jr. | H04M 3/42068 718/102 |

(Continued)

*Primary Examiner* — Roland J Casillas
(74) *Attorney, Agent, or Firm* — Patterson + Sheridan, LLP

(57) ABSTRACT

Techniques are disclosed for automatically adding accessibility properties to an application. One embodiment includes a method for adding accessibility. The method includes, for at least a first interface control provided by a first software application, the first interface control including a set of one or more accessibility properties: determining a control type of a plurality of control types based on one or more attributes of the first interface control, and associating the control type with the set of accessibility properties of the first interface control. The method further includes matching at least a second interface control provided by a second software application to one of the plurality of control types based on one or more attributes of the second interface control, the second interface control not including accessibility properties. The method further includes adding accessibility properties to the second interface control based on accessibility properties of the matched control type.

20 Claims, 5 Drawing Sheets

(56) References Cited

U.S. PATENT DOCUMENTS

| | | | | |
|---|---|---|---|---|
| 2002/0171677 | A1* | 11/2002 | Stanford-Clark | G06F 8/38 715/738 |
| 2003/0067488 | A1* | 4/2003 | Rudd | G06F 3/0481 715/765 |
| 2004/0218451 | A1* | 11/2004 | Said | G06F 3/0481 365/222 |
| 2005/0149206 | A1* | 7/2005 | Krane | G06F 9/451 700/17 |
| 2006/0139312 | A1* | 6/2006 | Sinclair, II | G06F 3/0481 345/156 |
| 2006/0168526 | A1* | 7/2006 | Stirbu | G06F 3/14 715/740 |
| 2006/0271637 | A1* | 11/2006 | McKeon | H04L 67/08 709/217 |
| 2007/0055938 | A1* | 3/2007 | Herring | G06F 17/30905 715/729 |
| 2007/0255569 | A1* | 11/2007 | Baker | G09B 21/001 704/270 |
| 2009/0007026 | A1* | 1/2009 | Scott | H04M 1/72588 715/865 |
| 2009/0055843 | A1* | 2/2009 | Engber | G06F 9/451 719/328 |
| 2009/0150787 | A1* | 6/2009 | Maehira | G06F 17/30899 715/733 |
| 2014/0340644 | A1* | 11/2014 | Haine | A61B 3/066 351/239 |
| 2016/0155069 | A1* | 6/2016 | Hoover | G06F 16/25 706/12 |
| 2017/0177166 | A1* | 6/2017 | Kockan | G06F 3/0481 |

* cited by examiner

ADDING ACCESSIBILITY PROPERTIES TO A SOFTWARE APPLICATION

CROSS-REFERENCE TO RELATED APPLICATIONS

This application claims priority to Indian Patent Application No. 201631025850, filed Jul. 28, 2016, which is hereby incorporated by reference in its entirety.

FIELD

The present disclosure relates to techniques for automatically adding accessibility properties to a software application.

BACKGROUND

A variety of software application and services may be made available to a user. For example, software applications may be made available as local client applications that are installed locally at a client device. Further, software applications may be made available to users over computer networks, such as the Internet. For example, software applications used to prepare and file income tax returns can be offered as a local client application or an online service.

Further, in the case of online services, a user may access the software applications via a variety of clients, including a web browser used to access a software application as a series of web pages, dedicated "thin" client applications, and so-called "apps" accessed using a mobile telephone or computing tablet.

In some cases, these software applications may not be accessible meaning they are not developed for accessible computing. Accessibility of a software application may refer to the ability of all people, regardless of a disability type or impairment (e.g., cognitive impairment, visual impairment, hearing impairment, motor and dexterity impairment, etc.) to be able to use or access the software application. In particular, developing accessible software applications may typically require a great deal of manual work and coding to ensure that the software application is accessible. Accordingly, many software applications may not be made accessible, thereby preventing many people from being able to access and use such software.

SUMMARY

One embodiment presented herein includes a computer-implemented method for adding accessibility to a software application. The method includes, for at least a first interface control provided by a first software application, wherein the first interface control includes a set of one or more accessibility properties: determining a control type of a plurality of control types based on one or more attributes of the first interface control, and associating the control type with the set of accessibility properties of the first interface control. The method further includes matching at least a second interface control provided by a second software application to one of the plurality of control types based on one or more attributes of the second interface control. The second interface control does not include accessibility properties. The method further includes adding accessibility properties to the second interface control based on accessibility properties of the matched control type.

Another embodiment presented herein includes a computing device for adding accessibility to a software application. The computing device includes a memory and a processor. The processor is configured to, for at least a first interface control provided by a first software application, wherein the first interface control includes a set of one or more accessibility properties: determine a control type of a plurality of control types based on one or more attributes of the first interface control, and associate the control type with the set of accessibility properties of the first interface control. The processor is further configured to match at least a second interface control provided by a second software application to one of the plurality of control types based on one or more attributes of the second interface control. The second interface control does not include accessibility properties. The processor is further configured to add accessibility properties to the second interface control based on accessibility properties of the matched control type.

Another embodiment presented herein includes a computing device for adding accessibility to a software application. The computing device includes, for at least a first interface control provided by a first software application, wherein the first interface control includes a set of one or more accessibility properties: means for determining a control type of a plurality of control types based on one or more attributes of the first interface control, and means for associating the control type with the set of accessibility properties of the first interface control. The computing device further includes means for matching at least a second interface control provided by a second software application to one of the plurality of control types based on one or more attributes of the second interface control. The second interface control does not include accessibility properties. The computing device further includes means for adding accessibility properties to the second interface control based on accessibility properties of the matched control type.

Another embodiment presented herein includes a computer-readable medium comprising instructions that when executed by a computing device cause the computing device to perform a method for adding accessibility to a software application. The method includes for at least a first interface control provided by a first software application, wherein the first interface control includes a set of one or more accessibility properties: determining a control type of a plurality of control types based on one or more attributes of the first interface control, and associating the control type with the set of accessibility properties of the first interface control. The method further includes matching at least a second interface control provided by a second software application to one of the plurality of control types based on one or more attributes of the second interface control. The second interface control does not include accessibility properties. The method further includes adding accessibility properties to the second interface control based on accessibility properties of the matched control type.

DETAILED DESCRIPTION

Figure 1:
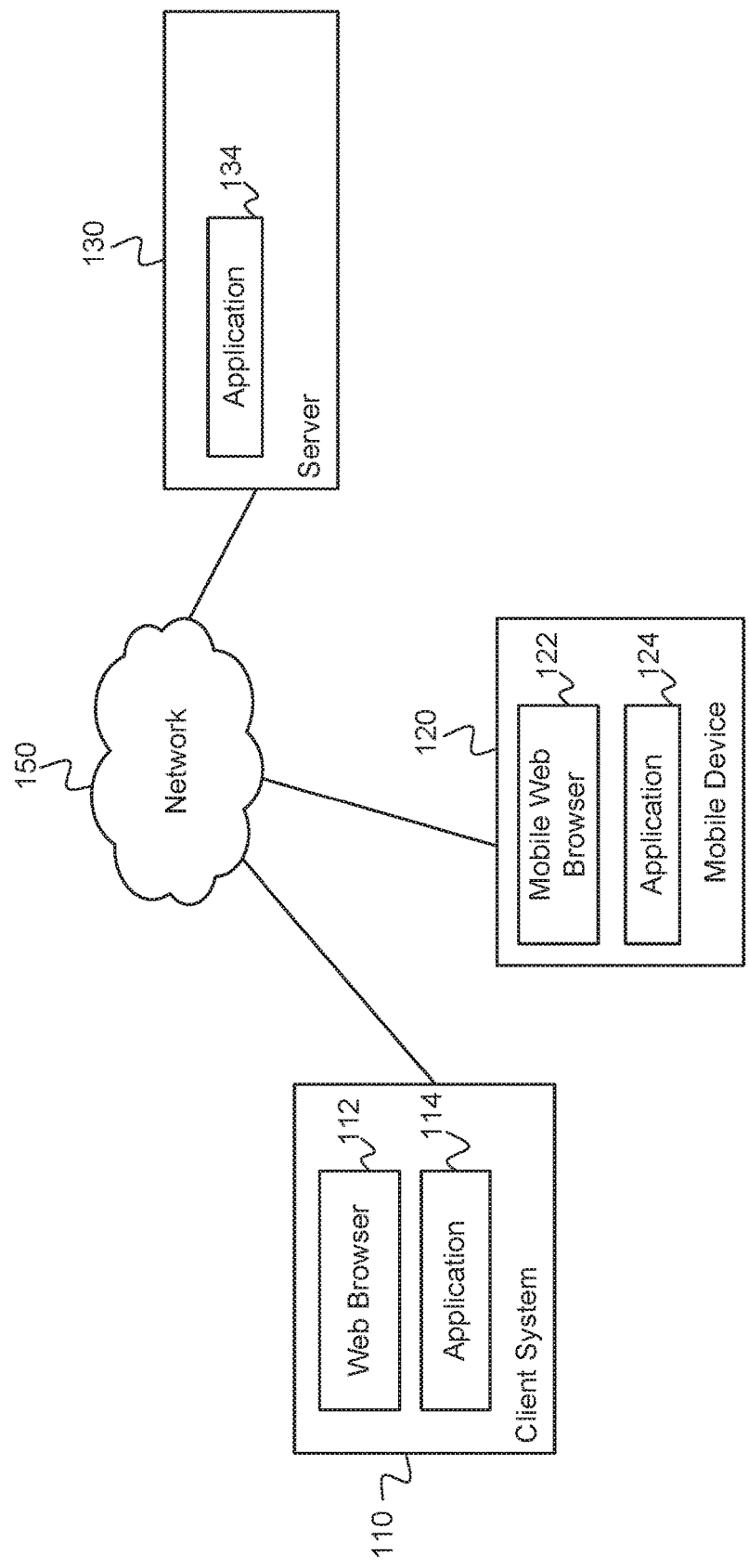
FIG. 1 illustrates an example of a computing environment used to access software applications, according to one embodiment.

Embodiments presented herein provide techniques for adding accessibility properties to software applications. For example, accessibility properties may be added to interface controls of software applications, without requiring a developer to manually add the accessibility properties to the interface controls of the software application. Accessibility features may be added to local client applications as well as applications accessed over a network as an online service, such as applications accessed by a local web browser, etc.

Software applications may include a variety of user interface controls, also referred to herein as controls. For example, an interface may include a variety of buttons, check boxes, list boxes, text boxes, dialog boxes, picture boxes, links, sliders, etc. Users may interact with these interface controls using a variety of input mechanisms, such as, a touchscreen, keyboard, mouse, voice input, etc. on a client device executing a software application. Each control may be associated with a collection of accessibility properties. These accessibility properties may include any type of information that can be used to enable accessibility of the control. For example, the information could include a textual description of a control, a textual description of an action associated with a control, a name of a control that may then be used by a text-to-speech component to synthesize speech audio that is output by the client device to the user, an automation ID, a textual description of a tool tip associated with the control, meta tags, etc. Accordingly, a visually impaired user can audibly receive information about the control in order to interact with the control.

Currently, accessibility properties for each control may need to be manually programmed by a developer of the software application. This can be time consuming and resource intensive. Therefore, many controls in software applications, or even entire software applications, may not be made accessible. Thus, an important portion of the population may not have access to such software applications.

Accordingly, some embodiments provide techniques to add accessibility properties to controls of a software application. In particular, a software application may already have some controls that have associated accessibility properties. However, the same software application, or another software application, may have similar controls that do not have associated accessibility properties. Accordingly, a computing device may then analyze the code of the software application and identify any controls that have associated accessibility properties (e.g., by searching the code and finding accessibility properties associated with the controls). The computing device may extract attributes of the controls as being associated with accessibility properties. For example, each control may have one or more attributes associated with it such as a class (e.g., button, check box, list box, text box, dialog box, picture box, links, slider, etc.), a color, a caption, a size, a font, a control name, automation ID, meta tags, tool tip text, etc.

Continuing, the computing device may classify each control identified as being associated with accessibility properties into a control type based on one or more of the attributes associated with it. In some embodiments, a control type may be associated with controls having a certain range of values (e.g., range of sizes, range of colors, range of words, etc.) for one or more attributes. Additionally, a control type may be associated with controls having particular values for one or more attributes. For example, a first control type may be associated with controls that have a class with a particular value (e.g., link) and have a caption with a range of words (e.g., e-mail, email, electronic mail, etc.) somewhere in the caption. Accordingly, a control with a class value of link and caption of "a link to e-mail" and another control with a class value of link and caption of "click to open electronic mail" may both be of the first control type.

In some embodiments, the computing device or another computing device may determine the plurality of control types for software applications (e.g., a single software application, related software applications (e.g., tax filing software), or unrelated software) using machine learning techniques with the controls of the software applications being used as the training data. In particular, the computing device may use the machine learning techniques to identify control types that accurately identify controls that share the same accessibility properties. For example, the computing device may determine that certain controls that share the same accessibility properties, have certain attributes (e.g., exact or within a range), and therefore identity a control type for controls with those certain attributes. The machine learning techniques may utilize one or more of Bayesian networks, deep learning, artificial neural networks, association rule learning, representation learning, similarity and metric learning, etc.

Further, the computing device may associate each control type with the accessibility properties of the controls of that control type. The computing device may utilize these control types with associated accessibility properties to add accessibility properties to controls of software applications without accessibility.

For example, the computing device may analyze the code of such a software application having controls that do not have associated accessibility properties and identify any controls without associated accessibility properties (e.g., by searching the code and finding controls without associated accessibility properties). The computing device may extract the attributes of the controls identified as being without accessibility properties.

Continuing, the computing device matches the controls identified as being without associated accessibility properties with a control type based on matching the attributes associated with each of the controls to the attributes of a control type. In particular, if a control has attributes that match with the attributes (e.g., exact attributes, range of attributes, etc.) of a control type (or match within a probability or match with a highest probability of the control types) the computing device may associate the control with that control type. Further, the computing device adds the accessibility properties associated with the control type to the code corresponding to the matching control for the software application. Accordingly, the computing device may automatically configure the controls of the software application that did not previously have accessibility properties to have appropriate accessibility properties.

Different aspects of these techniques are described in more detail herein, along with additional examples of how the techniques may be used to add accessibility properties to software applications.

FIG. 1 illustrates an example of a computing environment 100 used to access software applications, according to one embodiment. As shown, the computing environment 100 includes client system 110, a mobile device 120, and a server 130, which are each connected to a network 150. The network 150, in general, may be a wide area network (WAN), local area network (LAN), wireless LAN (WLAN), personal area network (PAN), a cellular network, etc. In a particular embodiment, the network 150 is the Internet.

Client system 110 is included to be representative of a general purpose computing system, such as a desktop or laptop computer hosting software applications that may be installed and run locally, or may be used to access applications running on the server 130. For example, client system 110 includes web browser 112 used to access the server 130 by rendering web pages (e.g., generated by the application 134) from or running applications (e.g., application 134) on the server 130. Similarly, client system 110 includes an application 114. The application 114 may be a local application that is installed and run locally on the client system 110. In another embodiment, the application 114 may be representative of a component of a client server application (or other distributed application) which can communicate with the server 130 over network 150. For example, application 114 may be a "thin" client where the processing is largely directed by the application 114, but performed by computing systems of the server 130 or a conventional software application installed on client system 110. Mobile device 120 is included to be representative of a variety of computing devices, such as a mobile telephone or computing tablet. As shown, the mobile device 120 may access the server 130 over network 150 using a mobile web browser 122 or local application or "app" 124 executed on the mobile device 120. In another embodiment, the app 124 may be a local application that is installed and run locally on the mobile device 120.

As shown, the server 130 includes an application 134 that may run locally on the server 130. Further, the application 134 may be accessed and executed by devices on the network 150, such as the client system 110 or the mobile device 120. The application 134, for example, may generate web pages that are rendered by a browser such as browser 112 or 122. In another example, application 134 may be accessed by or work along with client side applications, such as applications 114 or 124, as discussed.

In some embodiments, accessibility properties may be extracted from and/or added to any of the discussed software applications, including web browsers 112, 122 and applications 114, 124, and 134 based on the techniques discussed herein. Such techniques may also be applicable to any other appropriate software application. Further, the techniques discussed herein may be performed by any suitable computing device, such as the client system 110, the server 130, or another suitable computing device. Such a computing device need not be accessible via the network 150.

Figure 2:
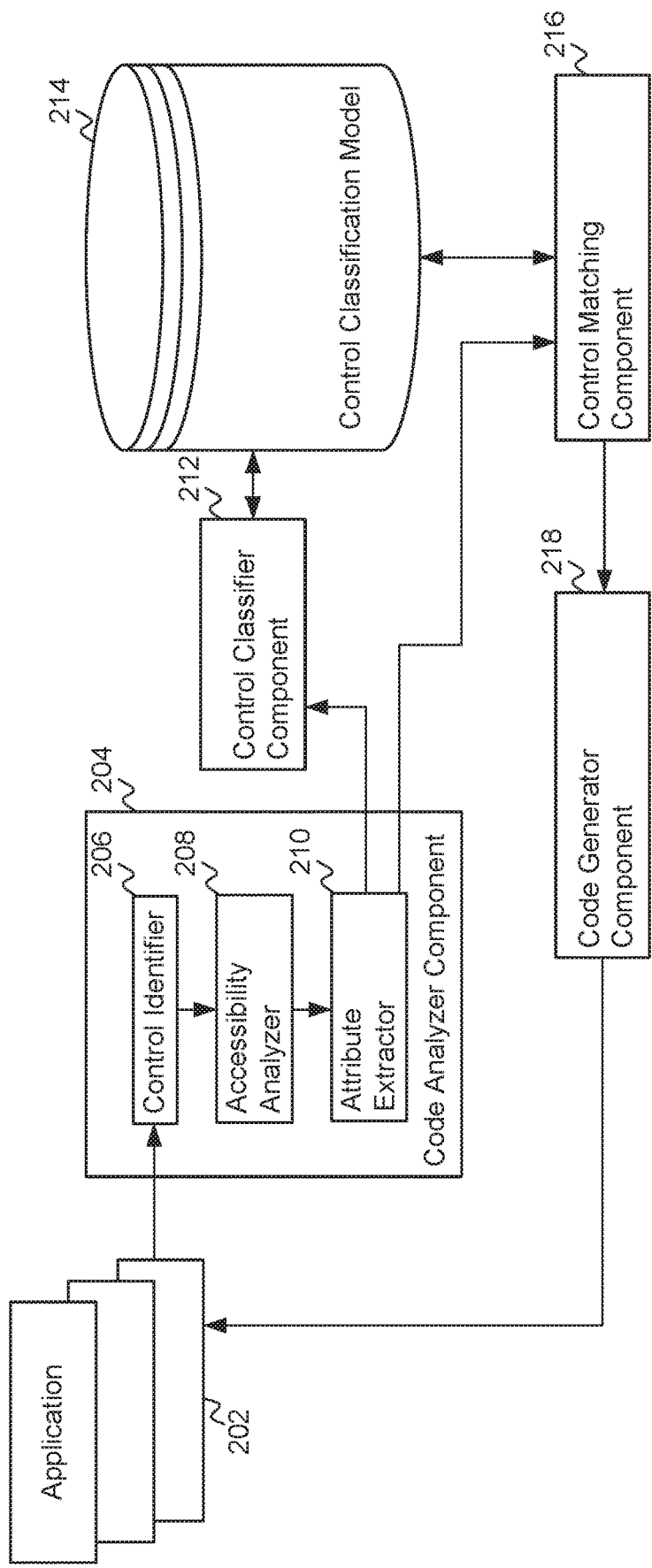
FIG. 2 illustrates components of a computing system for adding accessibility properties to a software application, according to one embodiment.

FIG. 2 illustrates components of a computing system for adding accessibility properties to a software application, according to one embodiment. Each component may be hardware, software, or a combination thereof. Each component may be a single software/hardware component, or may be distributed as multiple software/hardware components. Further, multiple components may be embodied as a single software/hardware component.

As shown, the code analyzer component 204 receives as input one or more applications 202 (e.g., the code associated with one or more applications 202). The code analyzer component 204 includes a control identifier 206 that identifies any controls in the applications 202. For example, each of the applications 202 may include interface controls that a user can interact with in the software application 202. The code analyzer component 204 may search the code for controls in the software applications 202.

Further, the code analyzer 204 includes an accessibility analyzer 208 that analyzes the identified controls in the applications 202 and determines which of the controls have accessibility properties associated with them, and which controls do not have accessibility properties associated with them. For example, the accessibility analyzer 208 may search the code of each control for accessibility properties associated with the control. The code analyzer 204 may additionally include an attribute extractor 210 that extracts attributes associated with each of the controls (e.g., both controls having associated accessibility properties and those not having associated accessibility properties). For example, the attribute extractor 210 may analyze the code of each control and extract the values of any attributes defined in the control.

The code analyzer component 204 may pass controls identified as having associated accessibility properties to the control classifier component 212 along with the extracted attributes for such controls. The control classifier component 212 may classify the controls into control types. Further, the control classifier component 212 may associate accessibility properties from the controls of a given control type with the control type itself.

For example, in some embodiments, some control types may be pre-defined (e.g., manually, using machine-learning techniques, etc.) and associated with attributes and particular values or ranges of values for the attributes. The control classifier component 212 may then assign the controls to control types based on the control having the same attributes (or having the most similar attributes) as those associated with the control type. In some embodiments, the control classifier component 212 may probabilistically (e.g., using Bayesian logic) assign controls to control types based on the attributes associated with the controls and the attributes associated with the control types. The control classifier component 212 may then associate accessibility properties from the controls of a given control type with the control type itself.

In some embodiments, the control types may be determined using machine learning techniques, where the controls identified as having associated accessibility properties are used as training data to identify appropriate control types. For example, the control classifier component 212 may utilize machine learning techniques to identify control types that accurately identify controls that share the same or similar accessibility properties. Accordingly, the control classifier component 212 may associate control types with attributes and particular values or ranges of values for the attributes based on the controls associated with that control type. The control classifier component 212 may then associate accessibility properties from the controls of a given control type with the control type itself.

The control classifier component 212 may generate a control classification model 214 that associates control types with attributes and accessibility properties. The control classification model 214 may be a database or model that includes information about the different control types as well as the attributes that define the control types, and any associated accessibility properties.

The code analyzer component 204 may pass controls identified as not having associated accessibility properties to the control matching component 216 along with the extracted attributes for such controls. The control matching component 216 may access the control classification model 214 and attempt to match any controls identified as not having associated accessibility properties to control types in the control classification model 214. For example, the control matching component 216 may try and match controls to control types based on the control having the same attributes (or having the most similar attributes) as those associated with the control type. In some embodiments, the control matching component 216 may probabilistically (e.g., using Bayesian logic) match controls to control types based on the attributes associated with the controls and the attributes associated with the control types.

The control matching component 216 may pass the information about the controls identified as not having associated accessibility properties, the control type for such controls, and the accessibility properties associated with such control types for such controls (e.g., stored in the control classification model 214) to the code generator component 218. The code generator component 218 may then take the accessibility properties from the control type associated with the control, and add it to the control (e.g., the code of the control). Accordingly, the code generator component 218 may add accessibility properties to controls identified as not having associated accessibility properties. The application may further be compiled and/or executed with the added accessibility properties.

Figure 3:
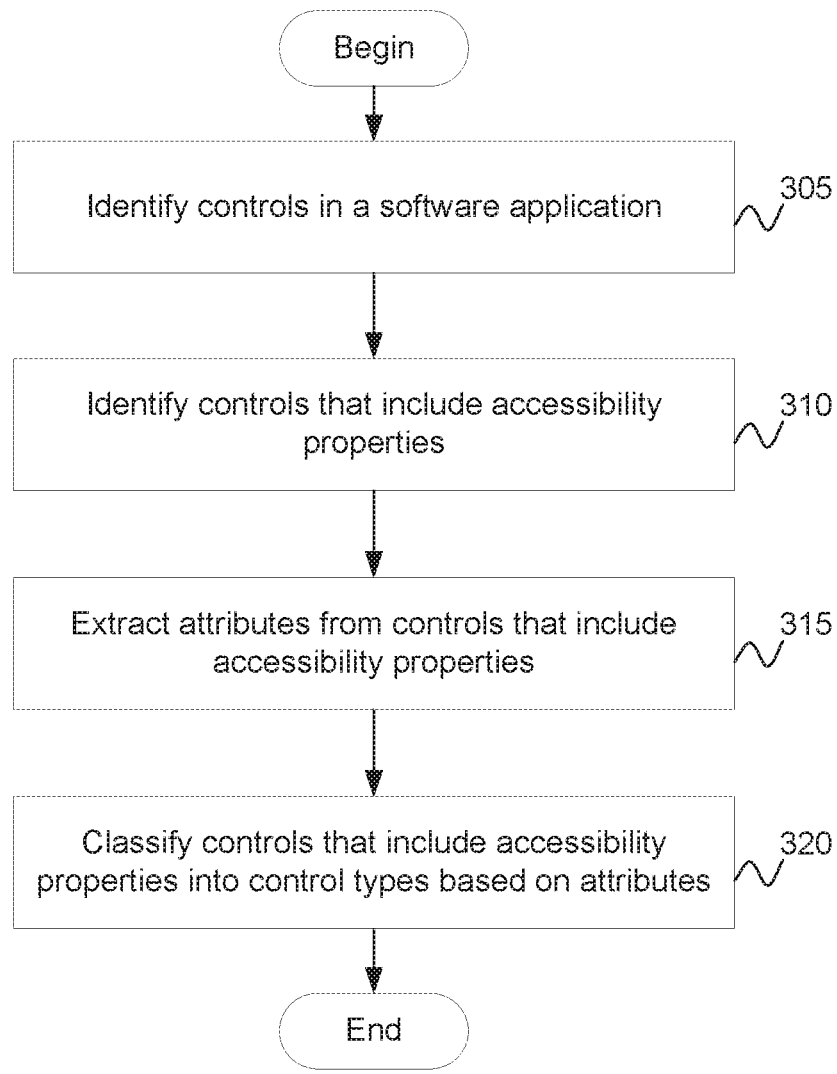
FIG. 3 illustrates a method for classifying controls that include accessibility properties into control types, according to one embodiment.

FIG. 3 illustrates a method 300 for classifying controls that include accessibility properties into control types. At 305, controls of a software application are identified. For example, a computing device may analyze the code of the software application and identify any controls in the code of the software application. Further, at 310, of the identified controls, the controls that include accessibility properties are identified. For example, the computing device may analyze the code of each of the identified controls, and determine if the code includes accessibility properties.

Continuing at 315, attributes associated with the controls that include accessibility properties are extracted. For example, the computing device may analyze the code of each of the controls having accessibility properties and extract the values of any attributes defined in the code of the control. Further, at 320, the controls that include accessibility properties are classified into control types based on the attributes associated with the controls, as discussed herein. For example, the computing device may classify the controls into control types based on machine learning techniques. In particular, the computing device may use the controls identified as having associated accessibility properties as training data to identify appropriate control types. For example, the computing device may utilize machine learning techniques to identify control types that accurately identify controls that share the same or similar accessibility properties. Accordingly, the computing device may associate control types with attributes and particular values or ranges of values for the attributes based on the controls associated with that control type. The computing device may then associate accessibility properties from the controls of a given control type with the control type itself.

Figure 4:
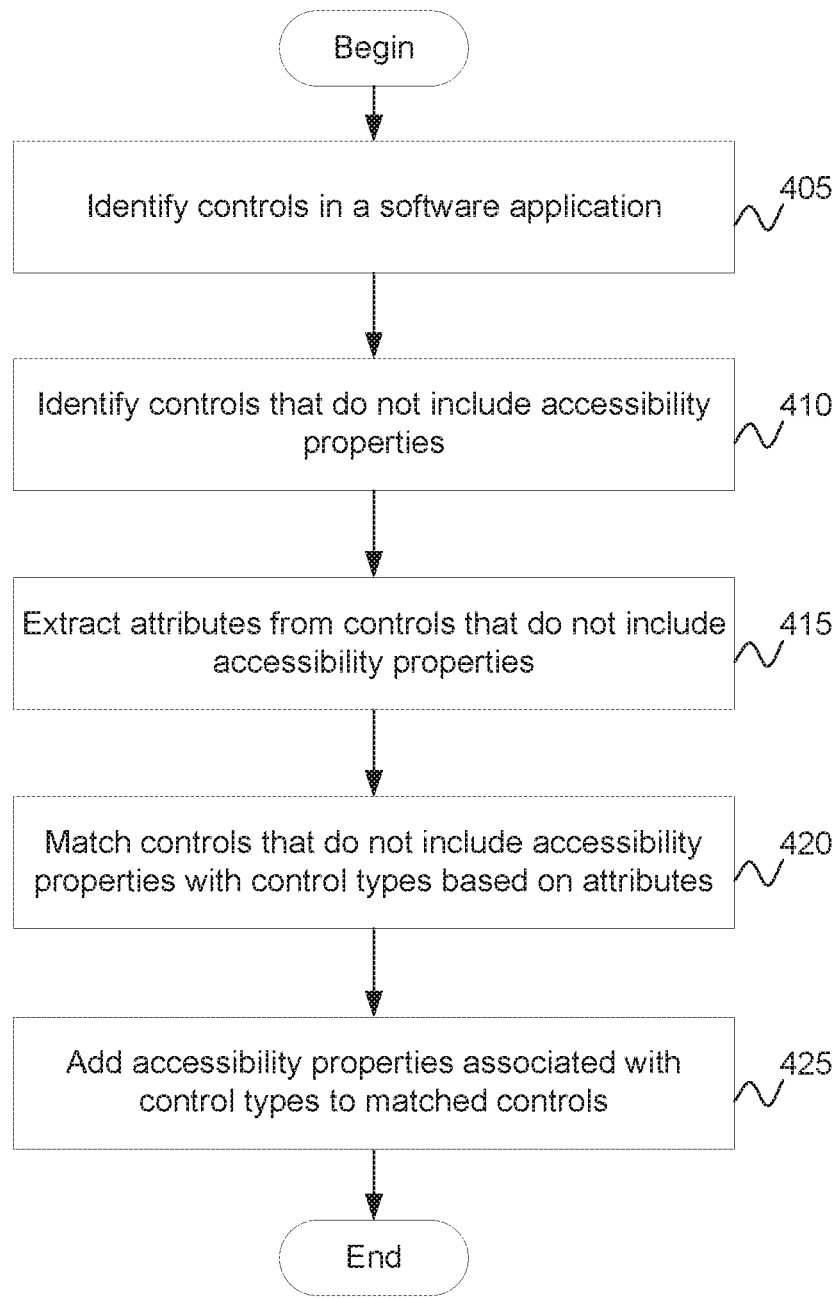
FIG. 4 illustrates a method for adding accessibility properties to controls that do not include accessibility properties, according to one embodiment.

FIG. 4 illustrates a method 400 for adding accessibility properties to controls that do not include accessibility properties, according to one embodiment. At 405, controls of a software application are identified. For example, a computing device may analyze the code of the software application and identify any controls in the code of the software application. Further, at 410, of the identified controls, the controls that do not include accessibility properties are identified. For example, the computing device may analyze the code of each of the identified controls, and determine if the code does not include accessibility properties.

Continuing at 415, attributes associated with the controls that do not include accessibility properties are extracted. For example, the computing device may analyze the code of each of the controls not having accessibility properties and extract the values of any attributes defined in the code of the control. Further, at 420, the controls that do not include accessibility properties are matched to control types that are associated with accessibility properties. For example, the computing device may match controls with control types based on the attributes associated with the controls being similar to or the same as attributes associated with the control types, as discussed herein.

At 425, accessibility properties are added to the controls that do not include accessibility properties based on the control type the control is matched with. For example, the computing device may add accessibility properties of the matching control type to the control of that control type.

Figure 5:
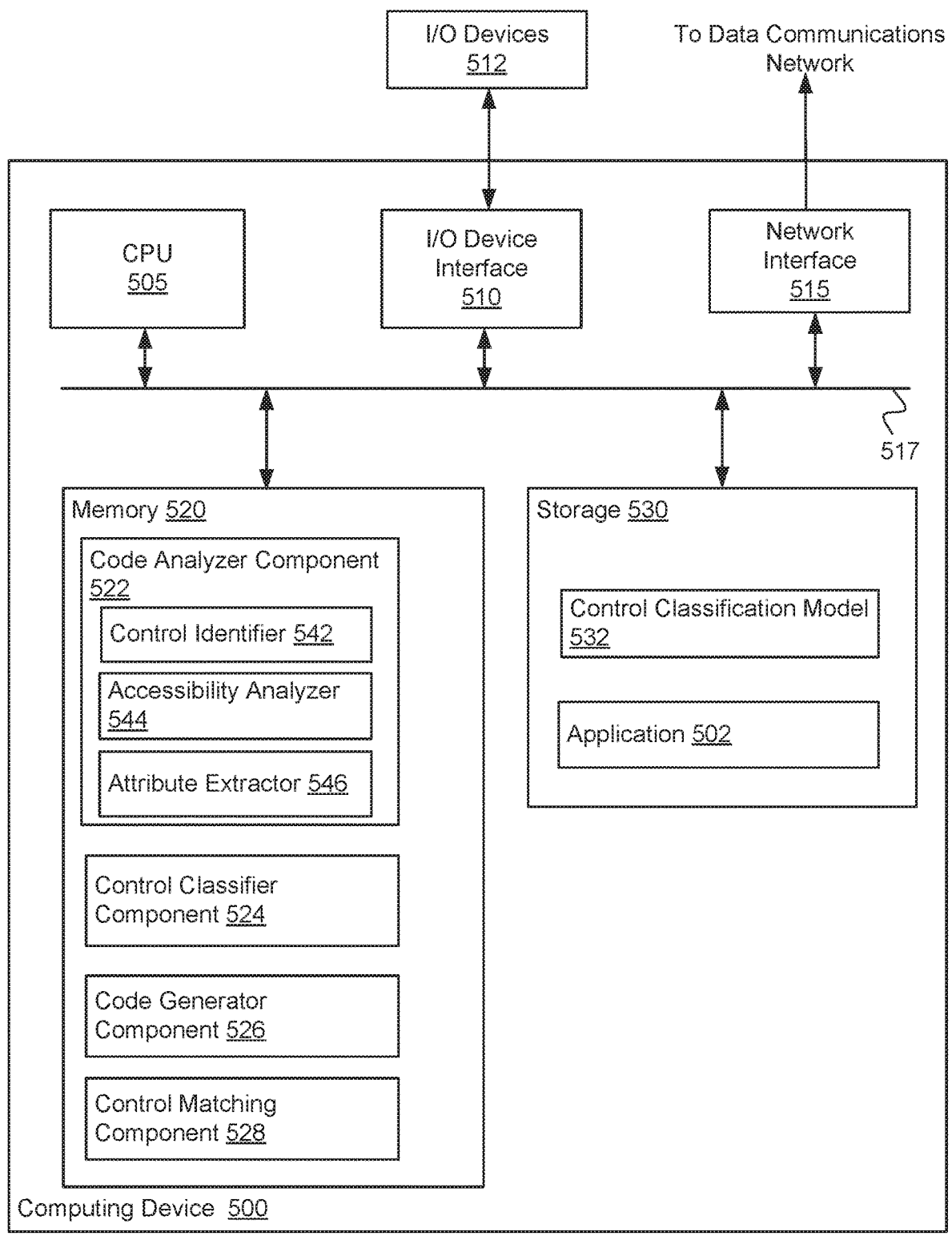
FIG. 5 illustrates an example computing system used to adding accessibility properties to a software application, according to one embodiment.

FIG. 5 illustrates an example computing system 500 used to add accessibility properties to a software application, according to one embodiment. As shown, the computing system 500 includes, without limitation, a central processing unit (CPU) 505, a network interface 515, a memory 520, and storage 530, each connected to a bus 517. The computing system 500 may also include an I/O device interface 510 connecting I/O devices 512 (e.g., keyboard, display and mouse devices) to the computing system 500. Further, the computing elements shown in computing system 500 may correspond to a physical computing system (e.g., a system in a data center) or may be a virtual computing instance executing within a computing cloud.

The CPU 505 retrieves and executes programming instructions stored in the memory 520 as well as stored in the storage 530. The bus 517 is used to transmit programming instructions and application data between the CPU 505, I/O device interface 510, storage 530, network interface 515, and memory 520. Note, CPU 505 is included to be representative of a single CPU, multiple CPUs, a single CPU having multiple processing cores, and the like, and the memory 520 is generally included to be representative of a random access memory. The storage 530 may be a disk drive or flash storage device. Although shown as a single unit, the storage 530 may be a combination of fixed and/or removable storage devices, such as fixed disc drives, removable memory cards, optical storage, network attached storage (NAS), or a storage area-network (SAN).

Illustratively, the memory 520 includes a code analyzer component 522, a control classifier component 524, a code generator component 526, and a control matching component 528. The code analyzer component may include a control identifier 542, accessibility analyzer 544, and an attribute extractor 546. The storage 530 includes a control classification model 532 and one or more applications 502. In some embodiments, these components may correspond to the components described with respect to FIG. 2.

As described, the code analyzer component 522 may be configured to analyze the code of applications 502 and identify any controls in the applications 502. Further, the code analyzer component 522 may identify which controls include accessibility properties and which controls do not. The code analyzer component 522 may further extract attributes associated with each of the controls.

The control analyzer component 522 may pass information about controls that include accessibility properties to the control classifier component 524. The control classifier component 524 may classify the controls into control types based on the attributes associated with the controls. Further, the control classifier component 524 may associate the accessibility properties of controls of a control type with the control type itself and store this classification model in the storage 530 as the control classification model 532.

The control analyzer component 522 may further pass information about controls that do not include accessibility properties to the control matching component 528. The control matching component may be configured to match the controls to control types associated with accessibility properties as defined in the control classification model 532. For example, the controls may be matched to control types based on comparing the attributes of the controls to the attributes of the control types and selecting a match based on matching the attributes of each.

The control matching component 528 may pass the information regarding the association between the controls that do not include accessibility properties and control types to the code generator component 526. The code generator component 526 may then add the same or similar accessibility properties from the control type associated with each control to the control itself, thereby adding accessibility properties to the controls of the application 502.

Note, descriptions of embodiments of the present disclosure are presented above for purposes of illustration, but embodiments of the present disclosure are not intended to be limited to any of the disclosed embodiments. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples a computer readable storage medium include: an electrical connection having one or more wires, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain, or store a program.

The flowchart and block diagrams in the Figures illustrate the architecture, functionality and operation of possible implementations of systems, methods and computer program products according to various embodiments of the present invention. In this regard, each block in the flowchart or block diagrams may represent a module, segment or portion of code, which comprises one or more executable instructions for implementing the specified logical function(s). In some alternative implementations the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

While the foregoing is directed to embodiments of the present disclosure, other and further embodiments of the disclosure may be devised without departing from the basic scope thereof, and the scope thereof is determined by the claims that follow.

What is claimed is:

1. A computer-implemented method for automatically adding control properties to a software application, the method comprising:
   for at least a first interface control provided by a first software component:
      determining a control type of a plurality of control types based on one or more attributes of the first interface control, and
      associating the control type with a set of one or more control properties of the first interface control,
      wherein the set of one or more control properties comprise one or more of a textual description of the first interface control, a textual description of an action associated with the first interface control, a name of the first interface control, an automation identifier, or a textual description of a tool tip associated with the first interface control;
   matching at least a second interface control provided by a second software component to one of the plurality of control types based on matching one or more attributes of the second interface control with one or more attributes of the one of the plurality of control types from the first interface control, wherein the second interface control does not include any control properties from the set of one or more control properties of the first interface control; and adding control properties from the one of the plurality of control types obtained from the first software component to the second interface control based on matching the second interface control to the one of the plurality of control types.

2. The method of claim 1, wherein the control properties from the set of one or more control properties comprise one or more of a textual description of a control, a textual description of an action associated with a control, or a name of a control.

3. The method of claim 1, wherein the plurality of control types comprises one or more of a button, a check box, a list box, a text box, a dialog box, or a picture box.

4. The method of claim 1, wherein the plurality of control types comprises one or more of a plurality of types of buttons, a plurality of types of check boxes, a plurality of types of list boxes, a plurality of types of text boxes, a plurality of types of dialog boxes, or a plurality of types of picture boxes.

5. The method of claim 1, wherein the one or more attributes of the first interface control comprise at least one of a class, a color, a caption, a size, or a font.

6. The method of claim 1, where the first software component and the second software component are different parts of a same software application.

7. The method of claim 1, wherein the plurality of control types are determined based on machine learning techniques that classify controls based on one or more attributes of the controls.

8. A computing device for automatically adding control properties to a software application, the computing device comprising:
  a memory; and
  a processor configured to:
    for at least a first interface control provided by a first software component:
      determining a control type of a plurality of control types based on one or more attributes of the first interface control, and
      associating the control type with a set of one or more control properties of the first interface control,
      wherein the set of one or more control properties comprise one or more of a textual description of the first interface control, a textual description of an action associated with the first interface control, a name of the first interface control, an automation identifier, or a textual description of a tool tip associated with the first interface control;
    matching at least a second interface control provided by a second software component to one of the plurality of control types based on matching one or more attributes of the second interface control with one or more attributes of the one of the plurality of control types from the first interface control, wherein the second interface control does not include any control properties from the set of one or more control properties of the first interface control; and
    adding control properties from the one of the plurality of control types obtained from the first software component to the second interface control based on matching the second interface control to the one of the plurality of control types.

9. The computing device of claim 8, wherein the control properties from the set of one or more control properties comprise one or more of a textual description of a control, a textual description of an action associated with a control, or a name of a control.

10. The computing device of claim 8, wherein the plurality of control types comprises one or more of a button, a check box, a list box, a text box, a dialog box, or a picture box.

11. The computing device of claim 8, wherein the plurality of control types comprises one or more of a plurality of types of buttons, a plurality of types of check boxes, a plurality of types of list boxes, a plurality of types of text boxes, a plurality of types of dialog boxes, or a plurality of types of picture boxes.

12. The computing device of claim 8, wherein the one or more attributes of the first control type comprise at least one of a class, a color, a caption, a size, or a font.

13. The computing device of claim 8, where the first software component and the second software component are different parts of a same software application.

14. The computing device of claim 8, wherein the plurality of control types are determined based on machine learning techniques that classify controls based on one or more attributes of the controls.

15. A non-transitory computer-readable medium having instructions stored thereon which, when executed by a computing device, cause the computing device to perform a method for automatically adding control properties to a software application, the method comprising:
  for at least a first interface control provided by a first software component:
    determining a control type of a plurality of control types based on one or more attributes of the first interface control, and
    associating the control type with a set of one or more control properties of the first interface control,
    wherein the set of one or more control properties comprise one or more of a textual description of the first interface control, a textual description of an action associated with the first interface control, a name of the first interface control, an automation identifier, or a textual description of a tool tip associated with the first interface control;
  matching at least a second interface control provided by a second software component to one of the plurality of control types based on matching one or more attributes of the second interface control with one or more attributes of the one of the plurality of control types from the first interface control, wherein the second interface control does not include any control properties from the set of one or more control properties of the first interface control; and
  adding control properties from the one of the plurality of control types obtained from the first software component to the second interface control based on matching the second interface control to the one of the plurality of control types.

16. The non-transitory computer-readable medium of claim 15, wherein the control properties from the set of one or more control properties comprise one or more of a textual description of a control, a textual description of an action associated with a control, or a name of a control.

17. The non-transitory computer-readable medium of claim 15, wherein the plurality of control types comprises one or more of a button, a check box, a list box, a text box, a dialog box, or a picture box.

18. The non-transitory computer-readable medium of claim 15, wherein the plurality of control types comprises one or more of a plurality of types of buttons, a plurality of types of check boxes, a plurality of types of list boxes, a plurality of types of text boxes, a plurality of types of dialog boxes, or a plurality of types of picture boxes.

19. The non-transitory computer-readable medium of claim 15, wherein the one or more attributes of the first interface control comprise at least one of a class, a color, a caption, a size, or a font.

20. The non-transitory computer-readable medium of claim 15, wherein the first software component and the second software component are different parts of a same software application.

\* \* \* \* \*